United States Patent
Nilsson

(10) Patent No.: US 9,358,082 B2
(45) Date of Patent: Jun. 7, 2016

(54) SYSTEM AND METHOD FOR PLANNING AND/OR PRODUCING A DENTAL PROSTHESIS

(75) Inventor: Urban Nilsson, Halta (SE)

(73) Assignee: NOBEL BIOCARE SERVICES AG, Zurich-Flughafen (CH)

( * ) Notice: Subject to any disclaimer, the term of this patent is extended or adjusted under 35 U.S.C. 154(b) by 591 days.

(21) Appl. No.: 13/509,472

(22) PCT Filed: Nov. 15, 2010

(86) PCT No.: PCT/EP2010/006929
§ 371 (c)(1),
(2), (4) Date: Jul. 24, 2012

(87) PCT Pub. No.: WO2011/057810
PCT Pub. Date: May 19, 2011

(65) Prior Publication Data
US 2012/0284000 A1    Nov. 8, 2012

(30) Foreign Application Priority Data
Nov. 16, 2009  (EP) .................................... 09014296

(51) Int. Cl.
*G06F 17/50* (2006.01)
*A61C 13/00* (2006.01)
(Continued)

(52) U.S. Cl.
CPC .............. *A61C 13/0004* (2013.01); *A61C 13/08* (2013.01); *A61C 8/0095* (2013.01)

(58) Field of Classification Search
CPC ............................ A61C 13/08; A61C 13/0004

USPC ........................................................ 703/1, 11
See application file for complete search history.

(56) References Cited

U.S. PATENT DOCUMENTS

| 4,663,720 A | 5/1987 | Duret et al. |
| 5,360,446 A | 11/1994 | Kennedy |

(Continued)

FOREIGN PATENT DOCUMENTS

| EP | 2254068 A1 | 11/2010 |
| EP | 2322115 A1 | 5/2011 |

(Continued)

OTHER PUBLICATIONS

International Search Report for PCT International Application No. PCT/EP2010/006929 dated Jun. 6, 2011.

(Continued)

*Primary Examiner* — Omar Fernandez Rivas
*Assistant Examiner* — Iftekhar Khan
(74) *Attorney, Agent, or Firm* — Knobbe Martens Olson & Bear, LLP

(57) ABSTRACT

A method, system and computer program of planning a dental prosthesis in a patient are disclosed, including steps, units or code segments for virtually planning a dental prosthesis. Envelope data is provided of an envelope guide, including data corresponding to a support surface for facial tissue, which is desired to result when the dental prosthesis is installed in the oral cavity of the patient. An outer envelope of a desired dental prosthesis in the oral cavity is simulated based on the envelope data. A desired dental restoration is provided and adjusted in a virtual environment relative to the simulated outer envelope, and dental prosthesis data is generated based on the adjusted desired dental restoration usable for producing the dental prosthesis.

37 Claims, 9 Drawing Sheets

(51) Int. Cl.
*A61C 13/08* (2006.01)
*A61C 8/00* (2006.01)

(56) References Cited

U.S. PATENT DOCUMENTS

| | | | |
|---|---|---|---|
| 5,725,376 | A | 3/1998 | Poirier |
| 5,768,134 | A | 6/1998 | Swaelens et al. |
| 5,810,592 | A * | 9/1998 | Daftary ................. A61C 8/005 433/172 |
| 5,816,810 | A | 10/1998 | Antonson et al. |
| 5,851,115 | A | 12/1998 | Carlsson |
| 5,857,853 | A | 1/1999 | Van Nifterick et al. |
| 6,319,006 | B1 | 11/2001 | Scherer |
| 6,814,575 | B2 | 11/2004 | Poirier |
| 6,994,547 | B1 * | 2/2006 | Sethi ...................... A61C 8/005 433/172 |
| 7,153,135 | B1 | 12/2006 | Thomas |
| 7,331,786 | B2 | 2/2008 | Poirier |
| 7,925,374 | B2 | 4/2011 | Andersson et al. |
| 8,026,943 | B2 * | 9/2011 | Weber .................. A61C 13/0004 348/135 |
| 8,029,277 | B2 * | 10/2011 | Imgrund et al. ............... 433/24 |
| 8,775,133 | B2 * | 7/2014 | Schroeder ........................ 703/1 |
| 2002/0015934 | A1 * | 2/2002 | Rubbert ................... A61C 7/00 433/29 |
| 2005/0170311 | A1 * | 8/2005 | Tardieu et al. .................. 433/76 |
| 2005/0277091 | A1 | 12/2005 | Andersson et al. |
| 2006/0040236 | A1 | 2/2006 | Schmitt |
| 2006/0127852 | A1 * | 6/2006 | Wen .............................. 433/213 |
| 2006/0127854 | A1 | 6/2006 | Wen |
| 2007/0128580 | A1 * | 6/2007 | Mormann .................. 433/201.1 |
| 2007/0154866 | A1 * | 7/2007 | Hall ............................... 433/213 |
| 2008/0193899 | A1 | 8/2008 | Karlsson et al. |
| 2009/0325125 | A1 * | 12/2009 | DiAngelo et al. ............. 433/173 |
| 2010/0099058 | A1 * | 4/2010 | Wang ............................ 433/173 |
| 2010/0151417 | A1 | 6/2010 | Nilsson et al. |
| 2010/0292963 | A1 * | 11/2010 | Schroeder ........................ 703/1 |
| 2011/0065065 | A1 * | 3/2011 | Mormann .................. 433/201.1 |
| 2011/0102549 | A1 * | 5/2011 | Takahashi ....................... 348/46 |
| 2011/0196524 | A1 | 8/2011 | Giasson et al. |
| 2012/0040311 | A1 | 2/2012 | Nilsson et al. |
| 2012/0095732 | A1 * | 4/2012 | Fisker et al. ....................... 703/1 |
| 2012/0123576 | A1 | 5/2012 | Pettersson et al. |
| 2012/0171635 | A1 | 7/2012 | Karlsson et al. |
| 2012/0183921 | A1 | 7/2012 | Karlsson et al. |
| 2012/0308962 | A1 * | 12/2012 | Kalinin ......................... 433/195 |
| 2012/0308963 | A1 * | 12/2012 | Hasselgren et al. ........ 433/201.1 |
| 2013/0209961 | A1 * | 8/2013 | Rubbert ............... A61K 6/0044 433/175 |
| 2013/0308843 | A1 * | 11/2013 | Tank ............................. 382/128 |

FOREIGN PATENT DOCUMENTS

| | | |
|---|---|---|
| WO | WO 2004/075771 A1 | 9/2004 |
| WO | WO 2004/098378 A2 | 11/2004 |
| WO | WO 2006/031096 A1 | 3/2006 |
| WO | WO 2007/117309 A2 | 10/2007 |
| WO | WO 2007/127804 A2 | 11/2007 |
| WO | WO 2007/134701 A1 | 11/2007 |
| WO | WO 2008/033893 A1 | 3/2008 |
| WO | WO 2008/083857 A1 | 7/2008 |
| WO | WO 2008/112925 A2 | 9/2008 |
| WO | WO 2008/145293 A2 | 12/2008 |
| WO | WO 2009/010543 A1 | 1/2009 |
| WO | WO 2009010543 A1 * | 1/2009 |
| WO | WO 2009/033677 A2 | 3/2009 |

OTHER PUBLICATIONS

International Preliminary Report on Patentability for PCT International Application No. PCT/EP2010/006929 dated May 22, 2012.
International Search Report for PCT Patent Application No. PCT/EP2010/006928 dated Feb. 1, 2011.
International Preliminary Report on Patentability for PCT Patent Application No. PCT/EP2010/006928 dated May 22, 2012.

* cited by examiner

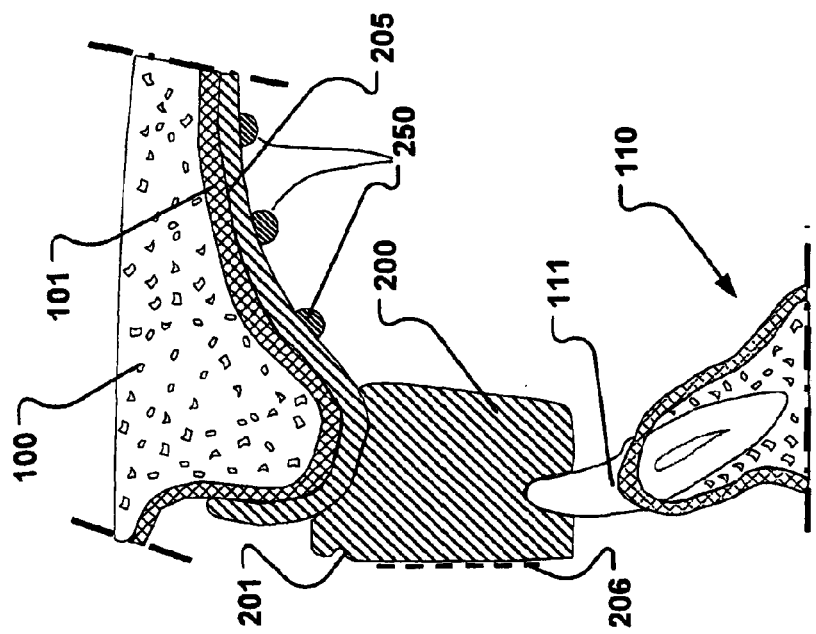
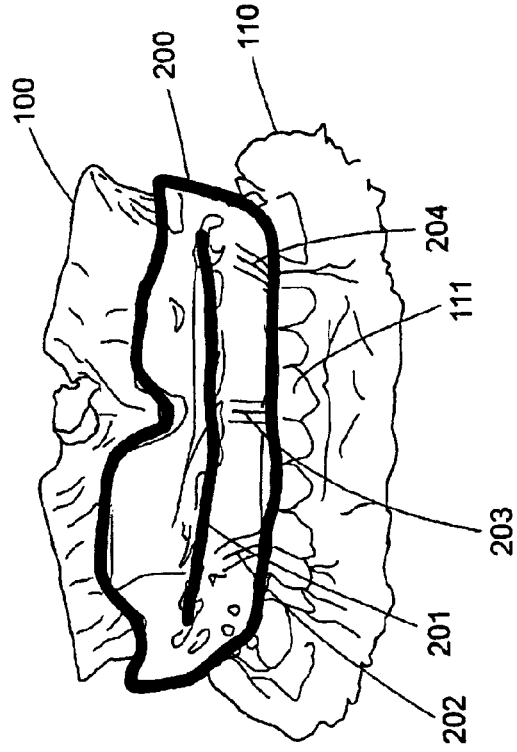
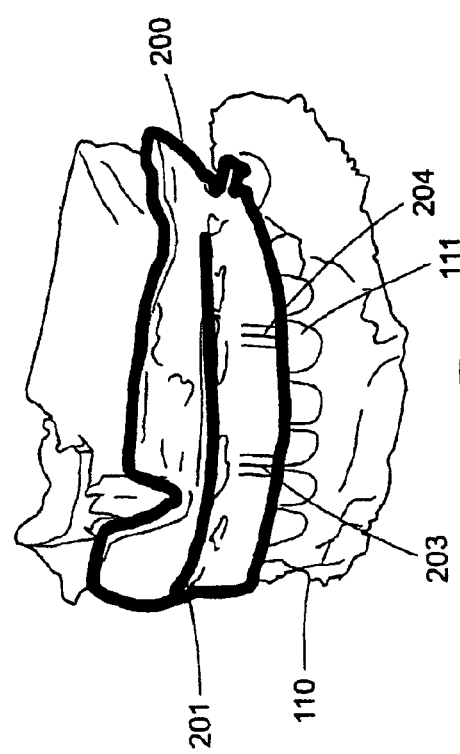

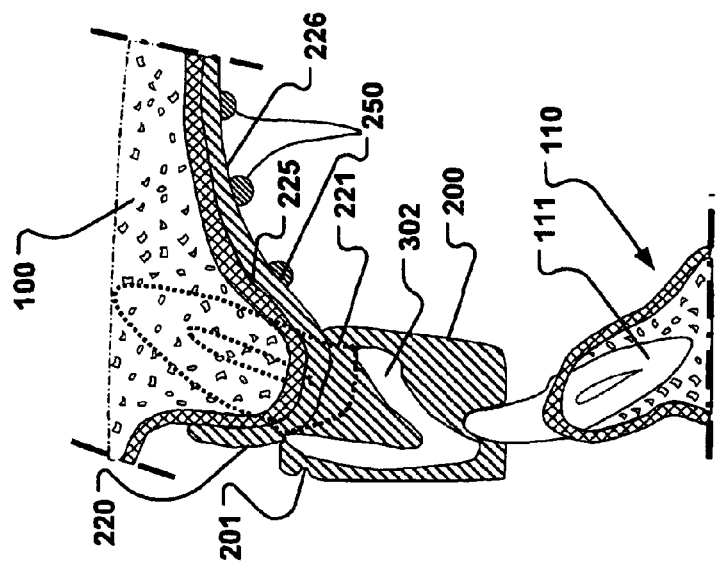
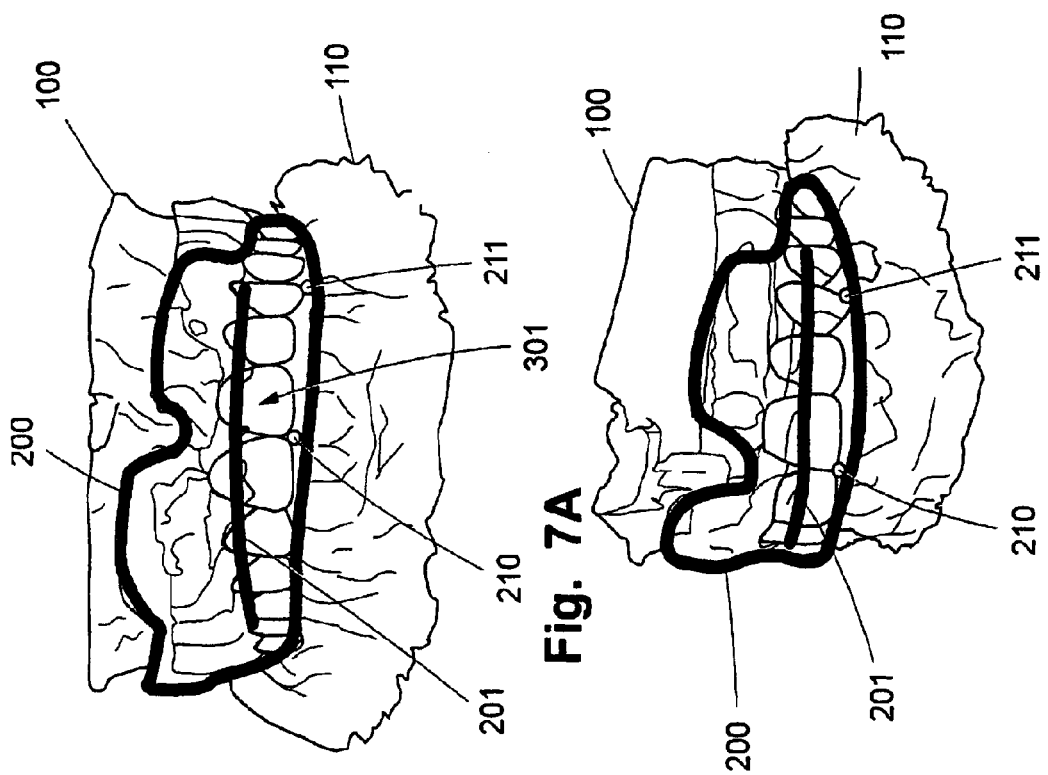

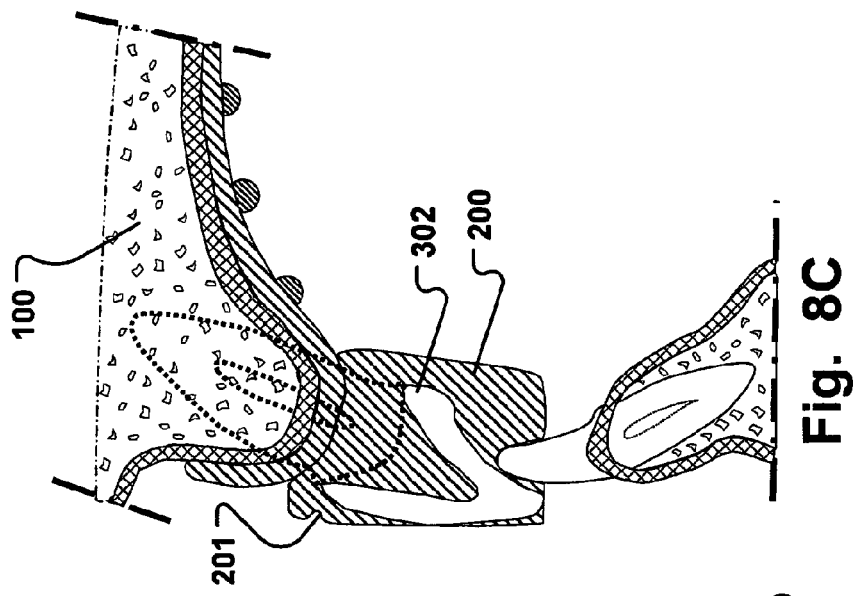
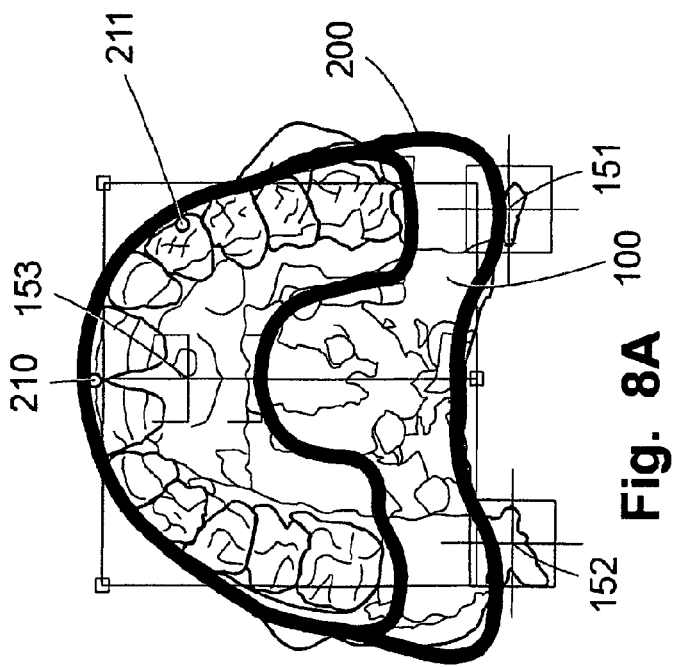
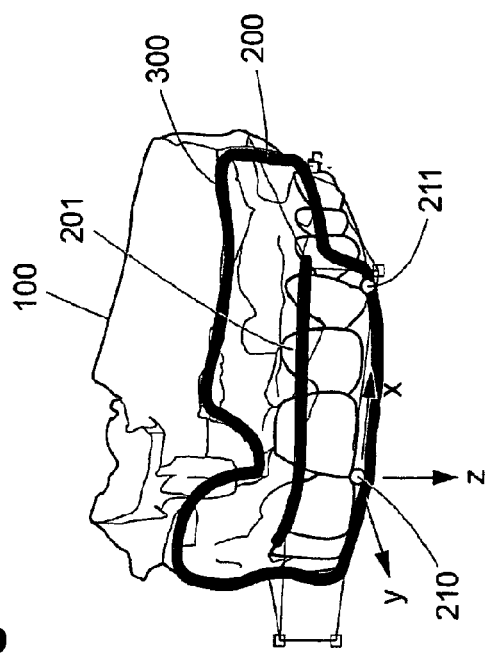

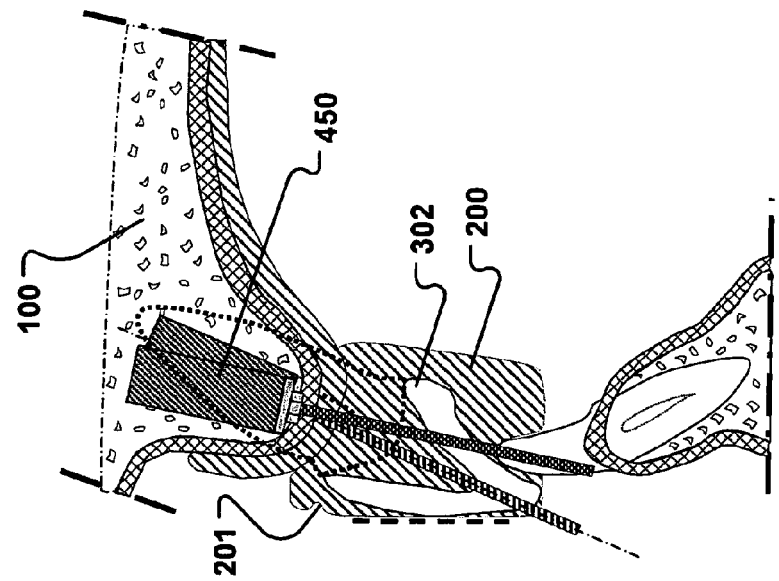
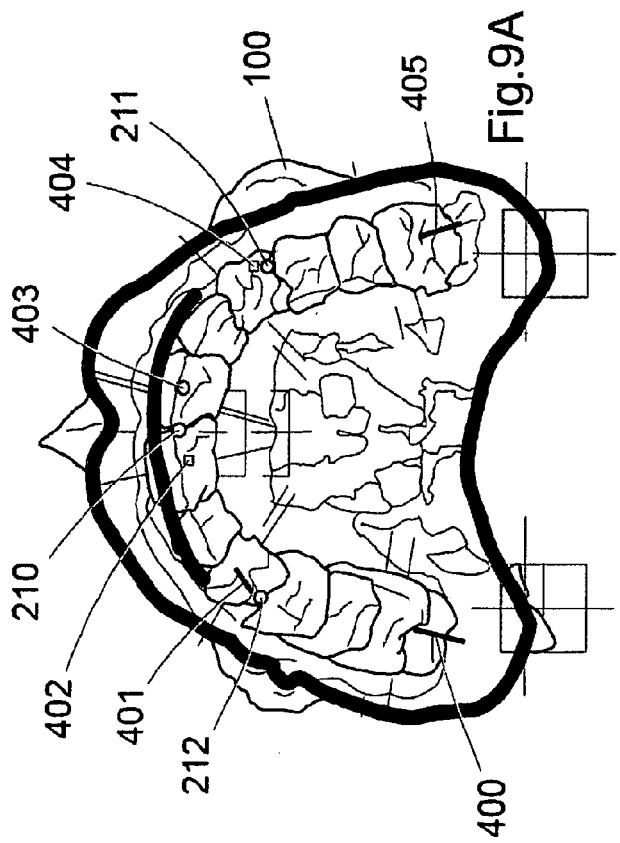
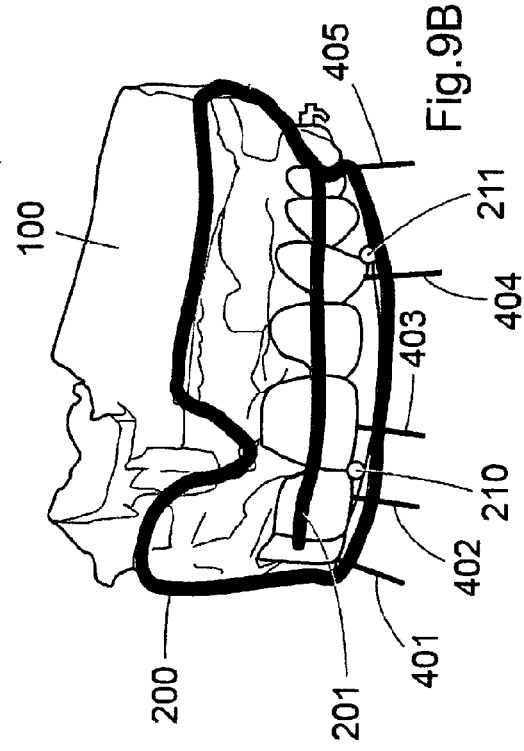

SYSTEM AND METHOD FOR PLANNING AND/OR PRODUCING A DENTAL PROSTHESIS

CROSS-REFERENCE TO RELATED APPLICATIONS

This application is a national stage application under 35 U.S.C. §371 of PCT Application No. PCT/EP2010/006929, filed on Nov. 15, 2010, which published in English as WO 2011/057810 on May 19, 2011, and which claims priority benefit of European Patent Application No. 09014296.9, filed on Nov. 16, 2009, the entire contents of which applications and publication are herein incorporated by reference in their entirety.

BACKGROUND

1. Field

This invention pertains in general to the field of digital dental design. More particularly the application relates to computer based virtual planning of dental restorations comprising dental prosthesis, as well as for methods of providing components for the dental restoration including a dental prosthesis, or components related to the dental prosthesis to be used during a dental restorative procedure, based on production data which is based on the virtual planning.

2. Description of the Related Art

In conventional dentistry, an impression of a region of interest in, or of the entire, oral cavity can be taken by means of an impression tray. From the impression a gypsum model of the lower jaw (mandibula) and the upper jaw (maxilla) can be cast by a dental technician for building a model of a desired dental restoration.

A wax appliance can be fit in the patient mouth for taking further measures and setting out certain desired landmarks in the oral cavity. Adjustments of the wax appliance can be made manually by the dentist when the wax appliance is inserted into the oral cavity of a patient. The wax appliance rests against the maxilla and/or mandibula, and can be used to mark, e.g., a central incisiory position, i.e., the dental midline or incisal line position between central incisor teeth, and a desired position of canines, as well as a desired smile line. The dentist can carve markings at the desired positions, when the wax appliance is installed in the patient. Further, a measure for the inclination of teeth in a dental restoration can be provided by carving the outer contour of the wax appliance that comes to rest against the lips.

Then, the dental technician receives the wax appliance in return. Based on the gypsum model, the wax appliance, which can be manually prepared in this manner, and using an articulator, the dental technician continues to manually prepare the dental restoration. A pre-denture can be prepared, e.g., as a dental wax-up, that corresponds to a model of the final restoration in the form of a denture. The pre-denture may for instance be put onto the soft-tissue of an edentulous jaw of the patient.

The dentist receives then this pre-denture in return, and the patient may need to be booked for another appointment, where the pre-denture is tried on by the patient and verified by the dentist. When the pre-denture is approved by the dentist, eventually with corrections, it is returned to the dental technician for preparing a final dental restoration.

However, this manual preparation using a wax appliance can have a number of disadvantages. For instance, it can be very time consuming, e.g., because the wax appliance may need to be sent back to the dental technician when the dentist has finished the patient specific adaptation. Furthermore, the precision of the final restoration may suffer. Many manual steps are a source of precision error, not at least due to the human factor. Consequences may be dire for the patient.

Hence, there is a need in some cases to provide a desired cost reduction in the preparation of dental prosthesis. The cost reduction could be achieved by reducing the number of manual steps.

Moreover, the range of possible products prepared by the dental technician may be limited. In addition, flexibility concerning adaptation and verification of dental restorations may be limited. When the dentist has carved too much material from the dental wax appliance, the process may need to be started all over again, and a new dental wax appliance may need to be prepared, the patient may need to be booked for multiple appointments, etc.

Known computer based methods, such as disclosed in U.S. Pat. No. 6,814,575 ('575), may still require such time consuming manual work. In '575 a denture is scanned that previously is prepared manually and has a fixed, manually determined teeth setup. Placement of dental implants is virtually planned, based on scan data of the patient's gum, jawbone and tissue structure, and of the manually prepared denture placed over the gum. The implants are positioned in jaw bone tissue based on a locked position of the scanned denture. Hence, the method disclosed in '575 is limited by fixed positions of the manually prepared denture. In FIG. 5 of '575 at position 39, false teeth of the reference denture are scanned. Based on this data, the implants' positions are chosen in the virtual planning. In FIG. 15 of '575 it is illustrated that an implant is adjusted, and the scanned and manually prepared denture (43, 44) is fixed. This computer based method thus lacks flexibility as it does not allow for a change of the teeth setup once the dental prosthesis is prepared, e.g., for taking into consideration a desired outcome of a dental restoration. Moreover, no data is provided to the technician manually preparing the denture, which is related to an appearance or position of facial tissue when the denture is placed over the gum. Thus, the final dental restoration, partly based on the denture, may not be optimal for the patient in terms of fit or aesthetics.

Hence, an improved method or system for virtually planning a dental prosthesis and/or for providing production data for a component related to the dental prosthesis based on the virtual planning can be advantageous and in particular allowing for increased flexibility, cost-effectiveness, versatility, patient comfort, and/or optimal calculation of dental prosthesis positions can be advantageous.

SUMMARY

Accordingly, certain embodiments preferably seek to mitigate, alleviate or eliminate one or more deficiencies, disadvantages or issues in the art, such as the above-identified, singly or in any combination by providing a method, a system and a computer program according to the appended patent claims.

Embodiments of the computer based virtual planning may take into consideration a desired result of a dental restoration on a comprehensive level. The desired result may for instance take into consideration such parameters as a desired orientation, or topography of facial tissue, both in rest and other positions of facial tissue, e.g., when smiling, in relation to a desired dental prosthesis. A real dental prosthesis may thus be produced based on dental prosthesis data derived by the virtual planning. A support surface of the dental prosthesis contributing to this desired orientation, or topography of facial tissue, may be provided on the buccal side of the dental prosthesis towards the facial tissue. The parameters of the desired dental prosthesis to provide this desired result may include e.g., a position of restorative teeth along the dental arch, a length and/or inclination of restorative teeth, etc. The desired result of the virtual planning can be based on a desired orientation of the support surface, which in turn can be based on data from an envelope guide, amongst others emulating this desired support surface. The term "envelope guide" used herein is defined in more detail below.

For this purpose, an envelope guide, which can be specifically prepared for a patient and adapted to the patient specific dental situation, can be digitized providing envelope data for the desired result of the dental restoration. The envelope guide can be adapted to physically emulate the desired result of the dental restoration in relation to facial tissue. The envelope guide may comprise an outer envelope portion having a support surface for the facial tissue. The outer envelope portion can be physically carved to process a surface corresponding to the desired result to be provided by the dental prosthesis. During virtual planning, data from this support surface may provide for an emulation of this support surface in a virtual environment. In this manner, an internal surface of facial tissue may be emulated in a desired rest position against the support surface. The facial tissue may be emulated both in rest and in other orientations, e.g., when smiling.

Thus, when digitized, envelope data can be provided based on the envelope guide. The envelope data can provide guidance for the virtual planning of a dental prosthesis in relation to the desired result when the prosthesis is installed in the oral cavity of the patient.

A dental prosthesis may thus be virtually planned, and produced from data based on that planning, which planned and produced prosthesis may be optimal for the patient in terms of fit, and/or aesthetics.

According to a first aspect of some embodiments, a computer-based method of virtually planning a dental prosthesis is provided. The method of planning a dental prosthesis may comprise providing scan data of an anatomical situation of an oral cavity of a patient; providing envelope data of an envelope guide, the envelope guide comprising an envelope portion having a support surface arranged to support facial tissue of the patient in a desired position when the envelope guide is positioned in the oral cavity of the patient; virtually simulating a dental prosthesis for supporting facial tissue in the oral cavity based on the scan data; from the envelope data, virtually simulating the support surface of the envelope portion with respect to the scan data of the oral cavity; virtually adjusting the dental prosthesis so that a surface of the simulated dental prosthesis corresponds to the simulated support surface of the envelope portion; and generating dental prosthesis data based on the virtually adjusted dental prosthesis, wherein the dental prosthesis data is usable for producing the dental prosthesis.

According to a second aspect of some embodiments, a computer-based system for virtually planning a dental prosthesis in a patient is provided. The system for planning a dental prosthesis may comprise a processing unit adapted to process scan data of an anatomical situation of an oral cavity of a patient. The scan data may be provided by a suitable scanning device or modality, which may be part of the system. The processing unit further is adapted to process envelope data of an envelope guide, the envelope guide comprising an envelope portion having a support surface arranged to support facial tissue of the patient in a desired position when the envelope guide is positioned in the oral cavity of said patient; virtually simulate a dental prosthesis for supporting facial tissue in the oral cavity based on the scan data; from the envelope data, virtually simulating the support surface of the envelope portion with respect to the scan data of the oral cavity, virtually adjust the dental prosthesis so that a surface of the simulated dental prosthesis corresponds to the simulated support surface of the envelope portion with respect to the oral cavity, and generate dental prosthesis data based on the virtually adjusted dental prosthesis, wherein the dental prosthesis data is usable for producing the dental prosthesis.

According to a further aspect of some embodiments, a method is provided of providing production data for a component related to the dental prosthesis. The method may comprise the method of the first aspect recited above and providing the dental prosthesis data as production data based on the virtual planning for producing at least a portion of the dental prosthesis or components related thereto.

According to yet another aspect of some embodiments, a computer program for virtually planning a dental prosthesis in a patient, for processing by a computer is provided. The computer program may comprise code segments for processing scan data of an anatomical situation of an oral cavity of a patient; processing envelope data of an envelope guide, the envelope guide may comprise an envelope portion having a support surface arranged to support facial tissue of the patient in a desired position when the envelope guide is positioned in the oral cavity of the patient; virtually simulating a dental prosthesis for supporting facial tissue in the oral cavity based on the scan data; from the envelope data, virtually simulating the support surface of the envelope portion with respect to the scan data of the oral cavity; virtually adjusting the dental prosthesis so that a surface of the simulated dental prosthesis corresponds to the simulated support surface of the envelope portion with respect to the oral cavity; and generating dental prosthesis data based on the virtually adjusted dental prosthesis, wherein the dental prosthesis data is usable for producing the dental prosthesis.

The desired dental prosthesis may comprise at least one of a virtual tooth or a simulated soft tissue surface. The simulated soft tissue surface is, for instance, a simulated external buccal gum surface, lingual gum surface or an gingival or palatal (internal) or lingual (external) gum surface of the desired dental prosthesis.

In certain embodiments, the computer program may be embodied on a computer-readable medium, and/or enables carrying out of a method according to the first aspect of the invention, and/or is implemented in a system of the above second aspect of the invention.

Further embodiments are defined in the dependent claims, wherein features for the second and subsequent aspects can be as for the first aspect mutatis mutandis.

Some embodiments can provide for consistent, predetermined results of dental design. Guesswork, as previously based on manual adjustments by several persons involved in the design and production process of dental prosthesis, can be eliminated.

Some embodiments can provide for facilitated virtual planning of dental restorations, in particular, in edentulous patients.

Some embodiments can provide for a more effective design of dental restorations, and some embodiments provide for increased flexibility of the dental design, as compared to the state of the art. Digitalization of patient anatomical situations and an envelope guide, such as provided in the form of a wax-plate, can provide for improved flexibility. The digital data thus available and provided for enabling a virtual environment can provide for versatility in an improved dental design, based on virtual planning of a dental restoration including components such as a dental prosthesis, e.g., having a bridge framework, and one or more dental implants.

Some embodiments can provide for improved precision of dental design, e.g., thanks to the minimized number of manual steps for planning and production of a dental prosthesis. Previously necessary manual steps, e.g., related to the use of a gypsum model, can be eliminated.

Some embodiments can provide for an optimized calculation of dental implants' positions in jaw bone tissue, e.g., with regard to patient fit, and/or aesthetics for instance related to important issues for the patient, such as a pleasant smile appearance when the dental prosthesis is installed in the patient.

Some embodiments can provide for iterative adjustment and verification of a dental design. This was not possible hitherto, e.g., as erroneous excessive carving from a wax-up appliance meant that the appliance had to be discarded and a new appliance had to be manually created in a time consuming manner.

Some embodiments can provide for improved time efficiency. Digital data may be sent from a dentist location to a dental technician location. The latter location may be remote. The dental technician may then produce a physical model for verification by the dentist. Alternatively, production of a dental model can be feasible at the location of the dentist. This procedure can be more time effective than the manual procedures of the state of the art.

Some embodiments can provide for more effective creation of aesthetically pleasing dental restorations. The patient may be provided with a dental prosthesis that supports facial tissue in a desired manner, e.g., to provide a pleasant smile.

Some embodiments can provide for a pre-visualization of dental restorations including soft tissue and facial tissue, which can be particularly advantageous for cosmetic cases.

Some embodiments can provide for increased patient case acceptance, e.g., thanks to reduced patient time at the dentist, exact fitting of restorations, reduced costs, satisfactory results of dental restorations with regard to aesthetic considerations, flexibility of planning of desired results, etc.

Some embodiments can provide for an increased number of various products or components that may be produced from production data based on virtual planning of a dental design. The products may include temporaries, dental bridge frameworks, surgical templates for drill guided dental surgery, etc. As intermediate steps, such as manual production of dental models, or digitization of such models, are reduced, the number of sources for errors may also be reduced, and precision of these dental prosthesis and products or components can be improved.

Some embodiments can provide for production data for making temporaries.

Certain embodiments can eliminate the need to consider or provide separate smile data, e.g., from a photography, which may be a procedure prone to errors.

An envelope guide in the context of the present application is adapted to be received in the oral cavity for a transfer of the desired features of a dental prosthesis, in particular, a support surface of the dental prosthesis for the facial tissue, such as lip tissue and/or cheek tissue. The envelope guide may have an envelope portion corresponding to a support surface for facial tissue, which support surface may be desired to result when the dental prosthesis is installed in the oral cavity of the patient. Based on this envelope portion, envelope data can be provideable for simulating at least part of the support surface, or outer envelope, of a desired dental prosthesis in the oral cavity.

The position of the facial tissue in a desired position can be physically registered by the shape of the envelope guide that is created in relation to the facial tissue and the anatomical situation of the oral cavity. The position of the facial tissue can be transferred to the envelope guide to simulate a result when a dental prosthesis is installed in the oral cavity of the patient. The buccal, or radially outward oriented, surface, i.e., the facial side of the envelope guide, is called an envelope portion, and specifically provides this surface information. Moreover, the envelope guide may comprise markings, e.g., for a desired position of specific teeth or teeth interspace, or facial tissue when not at rest, e.g., in the form of a desired smile line. The smile line can define a line of how large of a portion of the teeth is visible when the patient smiles. Further, the smile line may provide if, and how large of a portion of the interdental papilla, i.e., a part of the gingiva in the interdental space, is visible when the patient smiles. Based on this desired smile line, smile line data can be provided for virtual planning of a dental prosthesis.

The envelope guide may be made of wax, polymer material, or a combination thereof, or similar malleable material which may allow an adaptation of the shape of the envelope guide for a transfer of design parameters such as facial tissue position.

This envelope guide is not to be confused with a diagnostic dental wax-up appliance, which is a model of a dental restoration, including a teeth setup, prepared from a wax material, e.g., by a dental technician, for diagnostic purposes, e.g., in the form of trial dentures or pre-dentures. The envelope guide is also not a bite plate from which only occlusion information is available.

The support surface, outer boundary, or outer envelope, of the envelope guide can be an outer envelope surface oriented substantially buccally, or radially outwards of the dental arch, towards facial tissue, such as lip tissue or cheek tissue. The outer envelope can be substantially oriented orthogonal to an occlusion plane of the patient. The outer boundary provides a support surface for the facial tissue. The outer boundary can be formed to a desired support surface for facial tissue, e.g., by carving or otherwise manipulating the shape of the envelope guide.

Moreover, markings may be made in the outer boundary for further parameters of the desired outcome of the dental restoration, i.e., spatial positions or extensions of desired structures are marked and provide data therefor, e.g., for a smile line, position of certain teeth along the dental arch, etc.

When the envelope guide is digitized, e.g., by means of surface scanners, X-ray imaging, or volumetric scanning including Magnetic Resonance (MR), and Computed Tomography (CT), this surface position and orientation, as well as parameter information can be available as envelope data for virtual planning of a dental prosthesis—at least as a guidance for improving the planning.

Embodiments will be described below with maxillary soft tissue, etc. but may equally be applicable to mandible, mandibular soft tissue, etc. or any dental arch and soft tissue related thereto.

It should be emphasized that the term "comprises/comprising" when used in this specification is taken to specify the presence of stated features, integers, steps or components, but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments, reference being made to the accompanying drawings, in which

FIGS. 4A, 4B, 4C are views similar to those of FIGS. 3A-3C, including an example envelope guide in the form of a wax plate for providing boundary information;

FIGS. 7A, 7B, 7C are views similar to those of FIGS. 4A-4C including example virtually positioned markers and virtually positioned teeth from a teeth library for a dental restoration;

FIGS. 8A, 8B, 8C are views similar to those of FIGS. 6, 7B, and 7C, including an illustration of example virtual adjustments of teeth positions in relation to boundary information based on the envelope guide;

FIGS. 9A, 9B, 9C are views similar to those of FIGS. 8A-8C, including examples of virtually planned positions of dental implants;

DETAILED DESCRIPTION OF CERTAIN EMBODIMENTS

Figure 1:
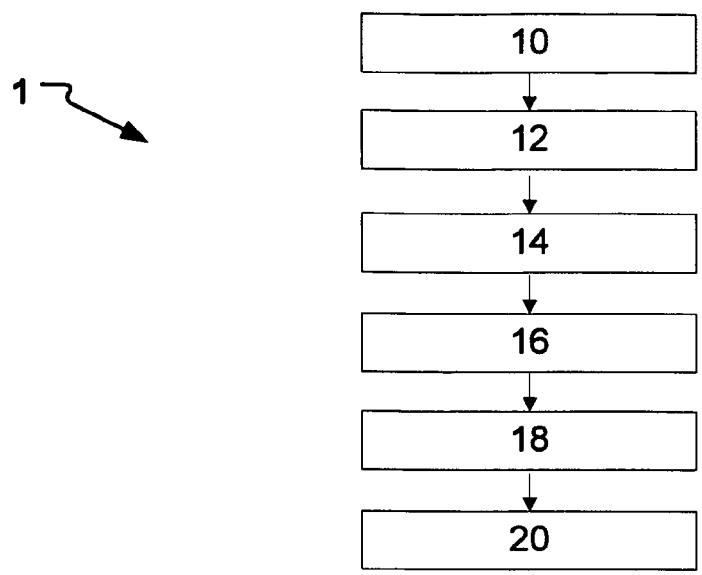
FIG. 1 is a flowchart of an example method of virtually planning a dental restoration and of producing elements for the dental restoration.

Specific embodiments will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope to those skilled in the art. The terminology used in the detailed description of the embodiments illustrated in the accompanying drawings is not intended to be limiting. In the drawings, like numbers refer to like elements. The envelope guide is shown transparent or unshaded in some of the figures for illustrative purposes only.

FIG. 1 is an example flowchart of a method 1 of virtually planning a dental prosthesis. The method 1 may also comprise planning of a dental restorative procedure including installation of the dental prosthesis planned using the method. The dental prosthesis may be installed in a real dental restorative procedure corresponding to the previously virtually planned procedure. During the procedure, a dentist may for instance use a surgical template produced from production data provided by the method of virtually planning the procedure.

In more detail, the embodied method 1 is an at least partially computer-based method of virtually planning a dental prosthesis in a patient.

The method 1 may comprise providing scan data 10 for an anatomical situation of an oral cavity of the patient; providing envelope data 12 of an envelope portion of an envelope guide corresponding to a support surface of a desired dental prosthesis for facial tissue, which provides for the facial tissue to be oriented in a desired result when the dental prosthesis is installed in the oral cavity of the patient; virtually simulating an outer envelope 14 of a desired dental prosthesis in the oral cavity based on the envelope data; and adjusting 18 the desired dental prosthesis relative to the outer envelope.

The desired dental prosthesis may comprise at least one of a virtual tooth or a simulated soft tissue surface. The simulated soft tissue surface is, for instance, a simulated external buccal gum surface 220, lingual gum surface 221, or an internal palatal gum surface 225 or an external palatal gum surface 226 of the desired dental prosthesis; see FIG. 7C.

The method may comprise providing at least one virtual tooth 16.

The method may also comprise creating the envelope guide in an oral cavity of the patient prior to providing the envelope data thereof in step 12. The envelope guide may be provided in a raw form, e.g., chosen from a number of pre-manufactured envelope guides. An envelope guide suitable for the specific patient can be chosen and positioned in the oral cavity of the patient such that it rests against the maxilla and mandibula along at least a portion of the dental arch. The envelope guide is then worked by the dentist in that position and a final envelope guide is created by adaptation to the specific patient. In particular, a patient specific buccal support surface for facial tissue, such as a lip support surface, can be created. Moreover, markings can be carved by the dentist during adaptation to the patient. Specific markings are described in more detail below.

In an embodiment, the method can comprise virtually planning the dental prosthesis based on a teeth-setup using a teeth library. The method can comprise providing at least one virtual tooth from said teeth library. The method can further comprise adjusting a position of at least one library tooth from the teeth library for the teeth-setup, such that the library tooth is located relative to an outer boundary defined by the envelope guide. The outer contour of the envelope guide can provide a rough estimate of the desired position of a final dental restoration and is used as an input in digitized form for guiding a precise planning of the dental restoration. The outer contour of the envelope guide thus can provide a target guide surface in relation to which a buccal orientation of a dental prosthesis of the dental restoration is aimed at.

The methods are described in more detail below, see in particular FIGS. 7C and 9C and the corresponding text below.

When production data is provided based on this virtual planning it may be used for producing dental prosthesis, elements or components related to dental restorations, as illustrated by step 20.

Figure 2:
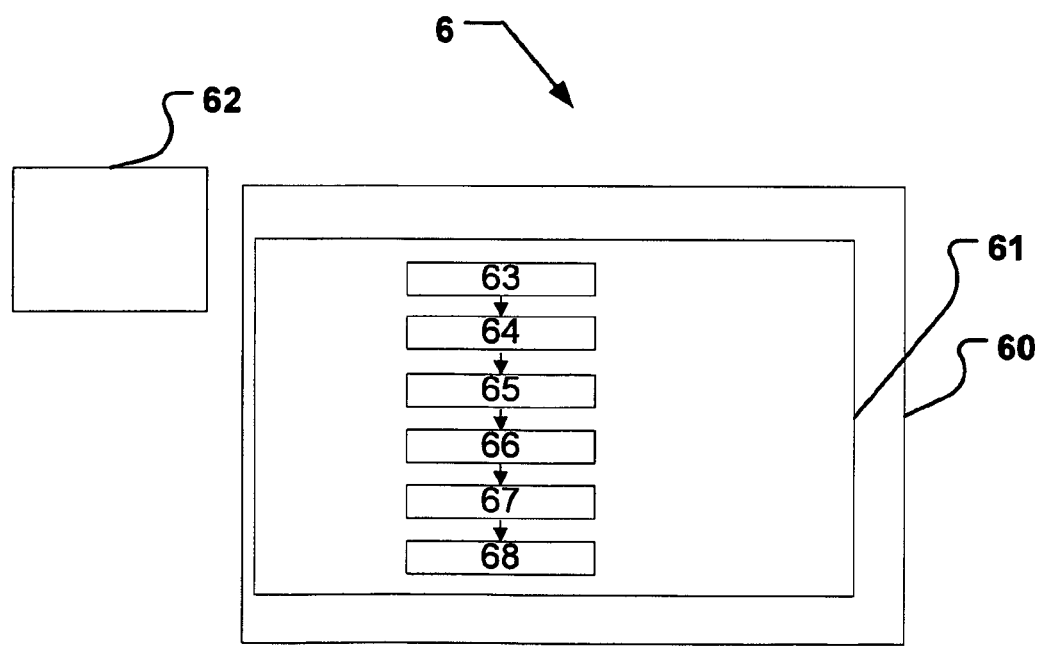
FIG. 2 is a schematic illustration of an example computer program and system.

FIG. 2 is a schematic illustration of an example computer program 61 and system 6 for implementing the method 1. The system 6 can be computer-based for virtually planning a teeth-setup based on a teeth library. The system can comprise a processing unit 62 adapted to adjust a position of at least one library tooth from the teeth library for the teeth-setup, such that the library tooth is located relative to an outer boundary defined by the envelope data of the envelope guide. The processing unit can be implemented to execute the computer program 61. The computer program 61 can be embodied on a computer-readable medium 60.

The computer program 61 can comprise a plurality of code segments, including a first code segment 63 to process scan data for an anatomical situation of an oral cavity of the patient. A second code segment 64 can process envelope data of an envelope guide, wherein the envelope data can comprise data of an envelope portion of the envelope guide. The envelope portion can correspond to a buccal support surface of a desired prosthesis for facial tissue, which provides for the facial tissue to be oriented in a desired position to result when the dental prosthesis is installed in the oral cavity of the patient. A third code segment 65 can simulate an outer envelope of the desired dental prosthesis in the oral cavity based on the envelope data. A fourth code segment 66 can provide at least one virtual tooth, which by a fifth code segment 67 can be adjusted relative to the simulated outer envelope.

The computer program 61 may comprise virtually planning a teeth-setup based on a teeth library, for processing by the processing unit 62 of the computer of the system 6. The computer program 61 can comprise in this embodiment the specific fifth code segment 67 to adjust a position of at least one library tooth from the teeth library for the teeth-setup in a virtual environment. In this manner the library tooth can be adjusted to be located relative to an outer boundary defined by the envelope guide.

Output data from the code segment 67 may provide production data in a code segment 68 for production of elements related to a dental restoration for implementing the virtually planned dental design in a real dental restoration.

The method, system and computer program are hereinafter described in further detail with reference to FIGS. 3-12.

Figure 3A:
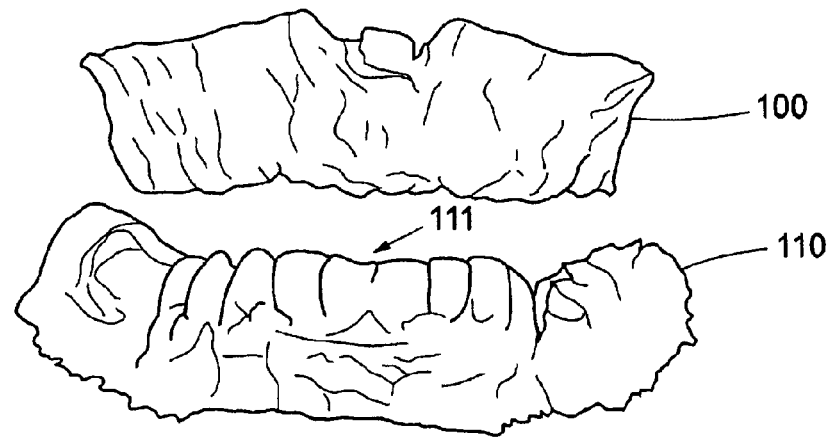
FIGS. 3A, 3B, 3C are a frontal perspective view, an elevated perspective view, and a cross sectional view, respectively, of portions of an example maxilla and mandibula in a virtual environment based on imported scan data.
Figures 3B, 3C:
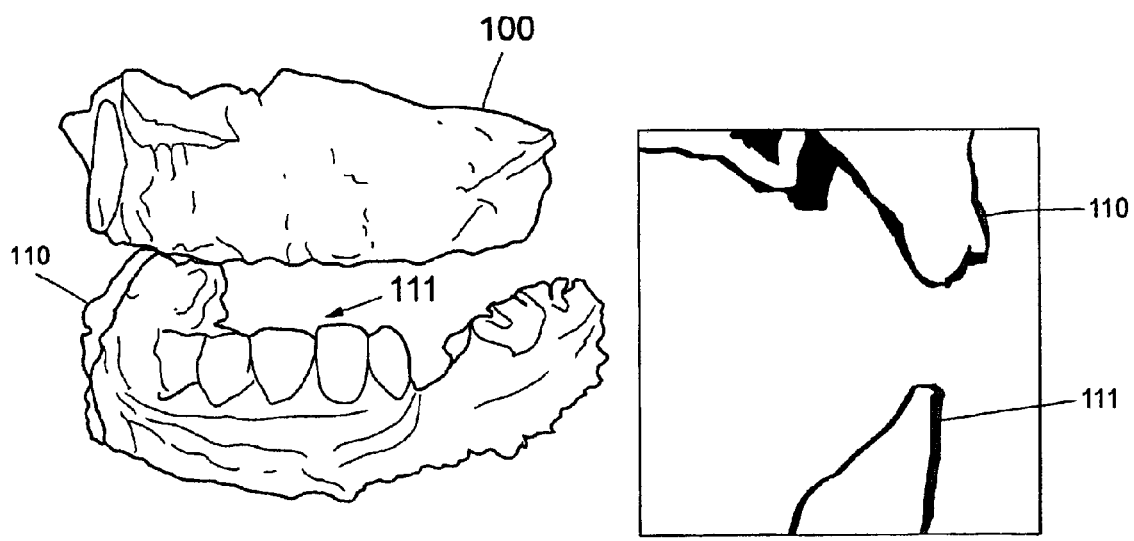

In FIGS. 3A, 3B, and 3C, portions of a maxilla 100 and a mandibula 110 are illustrated in a virtual environment based on imported scan data. The scan data provides information for an anatomical situation of a patient. The scan data may, for instance, be provided from X-ray, volumetric scanning, such as MR, CT, and/or surface scanned impressions. The scan data can provide information for jaw bone tissue and soft tissue of an oral cavity of the patient. For instance, impression tray based scanning can provide scan data for an outer surface of gingival soft tissue, and/or remaining teeth, and e.g., CT-scanning, can provide scan data for the jaw bone tissue. The combined data may be merged into a single scan data representing the anatomical situation, which is for instance described in European patent application EP09006665.5 or international PCT application WO2008/083857 of the same applicant as the present application, which are incorporated herein by reference in their entirety for all purposes.

It should be observed that the data derived from using impression trays may not provide information concerning a desired outcome of a dental restoration of this patient. The anatomical data may only comprise information of the anatomical situation as such. Information or data elements related to facial tissue, like lip tissue or cheek tissue, may not be possible to provide in the impression tray based scan data, as an impression tray usually extends out of the oral cavity when the impression is taken and thus the facial tissue may be pushed away from a rest or smile position thereof. However, information for the factual anatomical situation of bone tissue and gingival tissue in the oral cavity may be provided with high precision when using an impression tray.

In the illustrative example of FIGS. 3A, 3B, 3C, an edentulous maxilla is illustrated, while the mandibula has remaining teeth 111.

FIGS. 4A, 4B, and 4C are similar views to those of FIGS. 3A-3C, including the anatomical representation based on scan data, and a representation of an example envelope guide 200 for providing boundary information. FIG. 4C is a schematic illustration showing the representation of the envelope guide 200, which is based on input data suitably generated from an envelope guide, e.g., by surface scanning, X-ray imaging, or volumetric scanning including MR, CT, the envelope guide 200.

The envelope guide 200 can be adjusted to the specific patient anatomy of the oral cavity. The envelope guide 200 can be put entirely in the patient's mouth for transferring information also in relation to facial tissue. The envelope guide 200 can be put in abutment with an anatomical structure of the oral cavity. Further, the envelope guide can have a surface that is substantially complimentary in shape to the specific shape of the oral cavity. A portion of an envelope guide can conform, for instance, to the ridge of the upper and/or lower jaw, such as illustrated in the example of FIG. 4C, where the upper portion 205 of the envelope guide 200 can have a shape complementary to the shape of the outer surface of the maxillary soft tissue 101 as well as to the bite portion of the mandibular tooth 111.

The envelope guide can be made of a material which allows adaptation of its external shape to the patient specific conditions, e.g., by removing material therefrom, and/or reshaping the material, and/or adding material, usually by a dentist in a dialogue with the patient in order to achieve a desired result with regard to facial tissue in relation to a dental restoration. In this manner, for instance, a desired lip support surface 206 can be created, as illustrated by the dashed line in FIG. 4C.

The envelope guide 200, when scanned, can provide for envelope data thereof. The envelope data comprises data of an envelope portion of the envelope guide. The envelope portion can correspond to a support surface for facial tissue, which provides for the facial tissue to be oriented in a desired result when the dental prosthesis is installed in the oral cavity of the patient. The support surface for the facial tissue may comprise the lip support surface 206, as illustrated by the dashed line in FIG. 4C.

Remaining portions of the envelope guide can provide for envelope data of the remaining portions thereof. For instance, as illustrated in the example, a portion of the envelope data can provide information for the shape of the outer surface of the maxillary soft tissue. Other portions may provide data related to an occlusion portion of the envelope guide 200 that is positioned adjacent and along the dental arch, as illustrated in FIG. 4C adjacent to the tooth 111. In this manner the envelope data of the envelope guide may have a fixed spatial relation for matching with the scan data, e.g., based on a common occlusion portion of the envelope guide and the oral cavity, or on a common outer surface of the maxillary soft tissue.

Figure 13A:
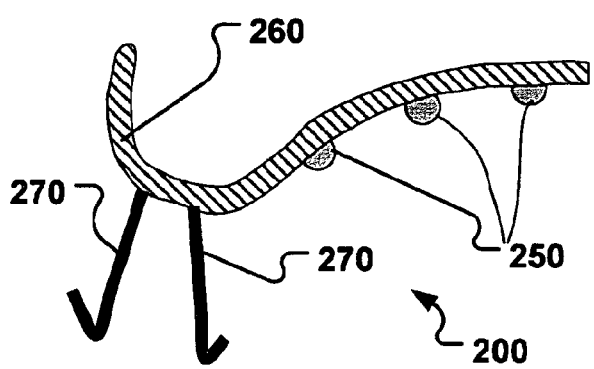
FIGS. 13A and B are schematic views of an example envelope guide having anchoring elements.
Figure 13B:
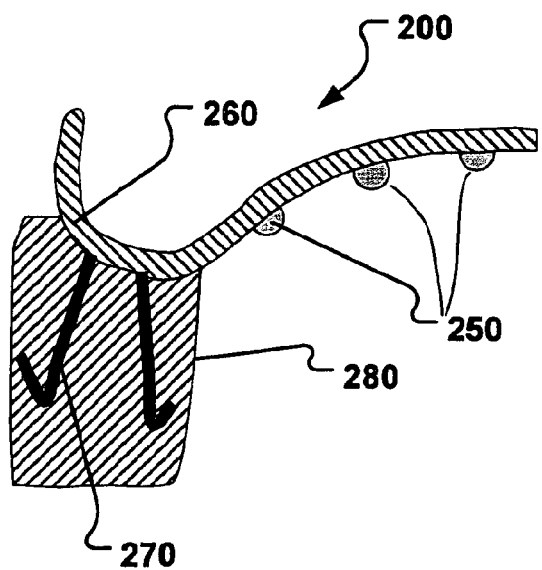

As shown in FIGS. 13A and 13B, the envelope guide 200 may be provided as a unit or an aggregate that is planned and/or produced at least partly based on anatomical scan data. The envelope guide 200 may be produced as a semi-manufactured article or as a finished product. The envelope guide 200 may comprise a framework 260 and a rim 280, such as made by wax, which is attached to the framework 260.

The framework 260 has an inner, palatal portion to be positioned against gum of the patient. Based on anatomical scan data, the inner portion may be made patient specific, which is advantageous for various reasons, including patient fit, patient comfort, etc. The framework 260 may be produced without the rim 280, which then is affixed thereto.

The framework 260 may be made of acrylic material. The framework 260 can be a stable portion to rest against the patient's gum The rim may be provided as a block that is manually adapted to a pre-manufactured framework 260. The rim can comprise the aforementioned envelope portion of the envelope guide 200. The rim may be affixed to the framework 260 by one or more anchoring elements 270 extending from the framework, such as illustrated in FIGS. 13A and 13B.

The framework 260 may be planned and produced in a similar manner as the dental prosthesis. A digitized outer soft tissue surface can provide for a corresponding inner surface of the framework 260. The opposing surface oriented to the inner of the oral cavity and towards the lip tissue, may be made by an offset from the soft tissue surface, to provide a Computer-Aided Design (CAD) object for the framework 260. This can provide for sufficient rigidity of the framework and a good patient fit.

The anchoring elements 270 may be produced in the same manufacturing process as the framework 260, e.g., by a rapid prototyping process. Alternatively, the anchoring elements may be affixed separately to the framework 260.

The anchoring elements 270 can extend in a first direction for anchoring the envelope portion. The anchoring elements 270 may further extend in a second direction along a portion thereof. This provides for improved fixation of the envelope portion, e.g., the rim 280, to the framework 260.

The anchoring elements may extend as protrusions from the framework. The protrusions may be provided as homogeneous objects. Alternatively, or in addition, a plurality of smaller objects may be provided as anchoring elements, facilitating attachment of the rim 280 to the framework 260, e.g., in the style of a hook and loop fastener.

The method 1 may comprise designing the framework 260 for the envelope guide 200, based on at least a portion of the scan data. The method may optionally include providing the framework 260 with at least one of the aforementioned anchoring elements 270 extending in a first direction for anchoring the envelope portion.

The framework 260 may be produced using a freeform technique, e.g., a 3D printer known from rapid prototyping techniques. This may be done at a dental laboratory.

The block 280 may then be affixed to the framework, e.g., in a dental laboratory. The block may be made of wax, but also of other malleable materials, such as a polymer material, or a combination thereof Alternatively, the framework may be produced without the anchoring elements.

Alternatively, the portion of the rim 280 may be produced together with the framework 260. The framework 260 and the rim portion may be made in a single integral piece. The framework 260 and wax rim portion may be made from the same material, e.g., by a rapid prototyping manufacturing method.

The framework 260 may be provided with fiducial markers 250. The fiducial markers 250 may be produced in the same manufacturing step as the framework 260 itself. For instance, the fiducial markers may be provided as air-filled cavities. The cavities may be produced in the rapid prototyping process.

The envelope guide can be converted to digital envelope data, which can be merged with the scan data to provide a model as shown in FIG. 4A-C for computer-based virtual planning of a dental restoration in the oral cavity.

The scan data, e.g., provided from an impression tray with fiducial markers, as described above, can comprise data for surfaces of the oral cavity. By scanning the impression tray both in the oral cavity and separately by surface scanning, and using the fiducial markers scanned in both scanning, the position of the surface of the oral cavity relative jaw bone tissue can be known. In turn, the envelope data of the envelope guide can have a fixed spatial relation to the scan data based on interfacing complementary surfaces of the envelope guide and the oral cavity. The complementary surfaces can be conforming, e.g., a bite portion of remaining teeth and the corresponding complementary surface in the envelope guide, or gum surfaces and corresponding complementary surface in the envelope guide. By surfacing scanning the envelope guide, the envelope data can comprise data for the complementary surfaces for which data is comprised in the scan data, allowing for a matching and subsequent merging of the envelope data and scan data.

In addition, or alternatively, the envelope guide may comprise fiducial markers, as illustrated in the example of FIG. 4C by the three spherical elements 250 arranged at the surface oriented towards the inside of the oral cavity at the portion of the envelope guide arranged at the soft tissue of the maxilla. By scanning the patient wearing such an envelope guide, e.g., with a CT scanner or cone beam CT scanner, the relation between the complementary surfaces may be determined in a similar manner as described above without the need of an impression tray.

The envelope data may be merged with the scan data based on known surface matching techniques for finding the complementary surfaces which are conforming. The envelope data may be surface matched based on the bite portion, and/or gum surfaces and corresponding complementary surface in the envelope guide.

The envelope guide 200 may comprise markings 201, 202, 203, 204 carved by the dentist during adaptation to the patient.

The markings may comprise, for instance, a first marking 201 for a desired smile line, which defines a line of how large a portion of the teeth is visible when the patient smiles. Further, the smile line may provide if and how large a portion of the interdental papilla is visible when the patient smiles. The first marking 201 thus may provide a measure for positioning and sizing virtual teeth correctly in relation to this desired result.

The markings further can comprise a second marking 203 for a central incisiory position, e.g., an incisal line position between central incisor teeth, also called a dental midline. The markings can further comprise a third marking 202 and a fourth marking 204 for desired positions of left and right canines in the envelope guide.

The markings 201-204 can be made based on experience of the dentist. The smile line may be marked in a dialogue with the patient, e.g., a low, average, or high smile line. The desired position of the smile line can be marked in the envelope guide and provides a basis for the choice of library teeth with regard to a length thereof. The central incisiory position, and desired position of canines can provide information to position teeth from a teeth library at a correct position along the dental arch. These markings can be taken advantage of in certain embodiments, as will be explained below.

Thus, the envelope guide can provide boundary information elements, amongst others for a spatial orientation of a lip support in rest, an extension of a smile line that is desired to be positioned in relation to the teeth, as well as information for an inclination and/or length of teeth, the position of a cementoenamel junction of such teeth, as well as a position of certain teeth along the dental arch. The cementoenamel junction can refer to a location of a tooth where the enamel meets the cementum, which covers the root of a tooth. In a dental prosthesis this can be the junction of the prosthetic tooth enamel to the prosthetic gingiva. Further, the position of interdental papilla may be provided by the boundary information elements based on the envelope guide.

Figure 5:
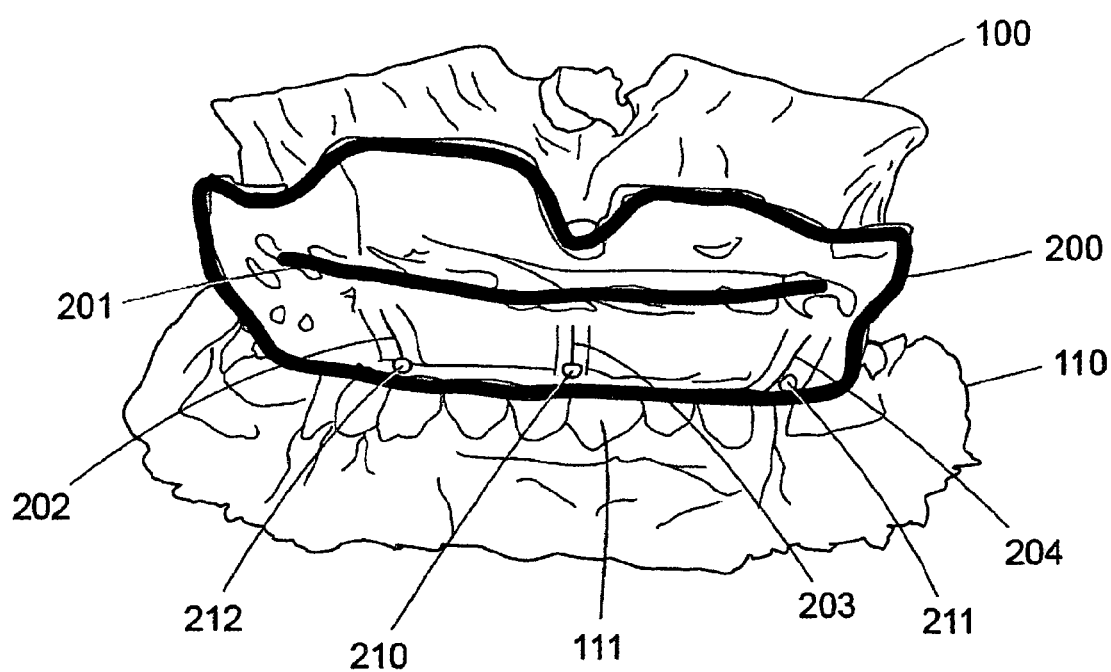
FIG. 5 is an example frontal perspective view similar to FIG. 4A, including virtually positioned markers.

FIG. 5 is a view similar to FIG. 4A, including virtually positioned markers 210, 211, 212, which can be positioned at the central incisiory position and the desired position of canines, respectively.

Virtually positioned markers can be used as fix points in space. Teeth from a teeth library are adjusted in relation to these fix points. The fix points can be created by marking points manually in the coordinate system of the graphical environment of the virtual planning system or software. The points can be marked in order to define where certain teeth are to be positioned. This can be made in order to become independent of the manner in which markings may be made in the envelope guide by the dentist. Each dentist may have a specific style for marking tooth design parameters, e.g., using various different carving tools, making markings differently deep, positioning the marking different in relation to an upper or lower edge of the envelope guide, etc. By providing the virtual markings during the virtual planning, mistakes or mix-ups of the position of teeth (tooth design parameters) based on the envelope guide, can be avoided.

The method of virtual planning thus can become less computational demanding and more reliable than in the case of automatically detecting the marked desired teeth positions in the envelope guide.

Furthermore, this may provide for a quicker way of setting up of the teeth set-up. In a practical example, e.g., the position in space of the coronal end of the left canine may be virtually marked to be at a first position, then the position of the central incisiory line may be virtually marked to be at a second position, etc.

The virtual markers 210, 211, 212 are illustrated as spherical markers, and may have other shapes, such as lines, cylinders, etc. The markers 210, 211, and 212 can provide more precise information for positions related to a desired position of at least one library tooth, such as a central incisiory position, and/or a desired position of canines, based on the more coarse markings 201-204 in the envelope guide 200.

Figure 6:
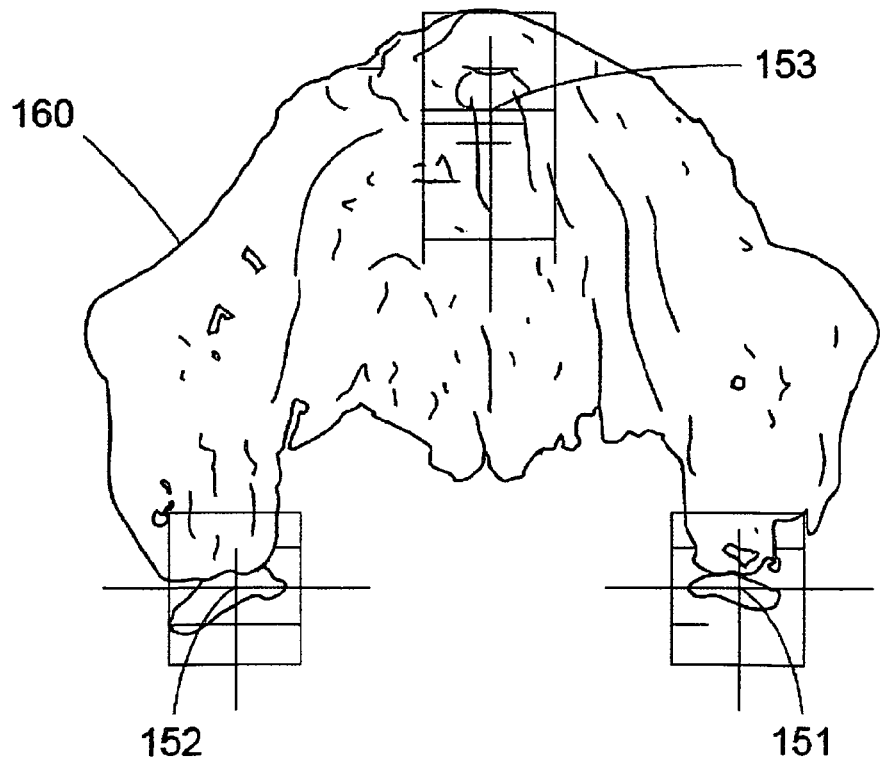
FIG. 6 is a perspective view from below of the edentulous maxilla of FIGS. 3-5 including virtually outlined anatomically fixed landmarks.

FIG. 6 is a perspective view from below of the edentulous maxilla 100 of FIGS. 3-5 including virtually outlined anatomically fixed landmarks 151, 152, and 153 in bone tissue 160. The landmarks 151, 152, and 153 may be used as anatomically fixed skull reference points for initially positioning one or more library teeth based on the anatomically fixed skull reference points prior to the adjusting of a position of the library tooth/teeth of a teeth setup.

The method may comprise in embodiments performing the virtually adjusting of the desired dental prosthesis in relation to an at least partly edentulous maxilla and/or mandibula of the patient.

A method of positioning library teeth from a teeth library is disclosed in WO2008/145293 of the same applicant as the present application, which is incorporated herein by reference in its entirety for all purposes. The method disclosed in WO2008/145293 may be based on anatomically fixed landmarks for determining the position of certain teeth along a dental arch in an edentulous jaw, and for determining an occlusion line.

Certain embodiments may further improve the positioning of the library teeth from that initial position, e.g., by taking into consideration a desired position of facial soft tissue for adjusting the initial position of library teeth accordingly. As explained above, the position of the library teeth may be adjusted with regard to inclination and/or a desired length. In addition, or alternatively, the tooth may be suitably chosen from the teeth library to have a desired position of a cementoenamel junction along such tooth. Further, the position of prosthetic interdental papilla may be chosen as desired, based on the aforementioned boundary information elements.

Thus, an anatomically and aesthetically correct teeth-setup can be provided in the virtual planning. Facial tissue when in rest against the teeth, when installed in the oral cavity of the patient—based on data from the virtual planning, can provide a desired aesthetically correct appearance of facial tissue and/or prosthesis relative to facial tissue. The final result may be simulated in the computer based virtual environment, and verified prior to producing elements for the final dental restoration.

Verification may, e.g., be made by a pre-denture produced from production data output from the virtual planning. The method of planning the dental restoration may comprise planning of teeth and planning implants. Other components like a surgical template or a bridge framework (which may be based on a library) can be provided. The bridge framework can be adapted to the virtual teeth and the soft tissue.

Based on this virtual planning, a dental prosthesis in a form of a pre-denture may be produced, e.g., by rapid prototyping techniques, in order to check if the virtual planning was done well. All data can be already available in the system and production data for the dental prosthesis, e.g., the pre-denture, is readily generated in the computer based environment. The pre-denture is provided for verification purposes prior to finalizing the virtual planning and producing the final dental prosthesis.

The pre-denture can be installed in the patient. The dentist may now check if the lip support is as desired, if the smile line is as desired, etc. The patient or dentist may now make changes in the virtual environment based on the information obtained from this verification.

The pre-denture may only be used during this verification, or the pre-denture may be a temporary prosthesis that is left in the patient until a final prosthesis is produced and ready for installation in the patient.

The pre-denture may, for instance, be a denture supported by the soft tissue, or the pre-denture may be supported by dental implants in the patient. In the latter case, a surgical template and the pre-denture may be produced. The dental implants can be installed in the patient using the surgical template. Then the pre-denture can be affixed to the dental implants. The correct fit of the dental prosthesis, now in a form of the pre-denture, can be checked and verified with the patient. In case the fit is fine, the final dental prosthesis can be produced and installed. In case the pre-denture reveals that the dental prosthesis is not satisfactory, the virtual planning can be adjusted based on the information obtained from this verification. As the dental implants are now installed in the patient, the connection interface of the dental implants towards the bridge framework can be locked in the virtual planning environment.

It should be noted that even if the virtual planning is re-started and the dental prosthesis is adjusted, all data can be already present in the computer based system. There is no need for acquiring further data. However, in certain embodiments continued virtual planning is only made of those parts of the dental prosthesis that are not locked.

In case the dental implants are not implanted at the desired position due to some practical reason, data for the connection interface of the dental implants at their actual position may be acquired. This may be done with an impression taken of the connection interface with an impression tray, scanning the impression tray, and matching against soft tissue in the computer environment to enter the data for the actual position and orientation of the implants. Now the dentist may adjust the virtual planning if desired. For instance the bridge framework may be adjusted, or the teeth may be adjusted.

An example initial positioning of a teeth setup 301 is illustrated in FIGS. 7A, 7B, and 7C. Initial positioning planning may be made manually, semi-automatically or automatically. The teeth setup 301 comprises a plurality of library teeth, such as a virtual tooth 302 shown in cross section in FIG. 7C. The library teeth are positioned at a suitable position along the crest to form a dental arch in the maxilla 100. Initial positioning may be made manually or automatically.

Automatically initial positioning may, for instance, be based on recognition of specific markers that are comprised in the envelope guide and positioned there by the dentist. For instance a specific shape and/or position of markers may be linked to a specific type of teeth for facilitating this automatic recognition, e.g., a triangular shape for a canine, a square shape for an incisor, etc.

Manual initial positioning or semi-automatic initial positioning may be based on the markers 210, 211, and 212. Alternatively, or additionally, the initial position in the dental arch may be based on the above mentioned anatomically fixed landmarks 151, 152, and 153; and/or experience of a dentist performing suitable manipulations in the computer based virtual environment.

As can be seen, the virtual tooth 302, as well as the remaining teeth of the teeth setup, can be positioned in relation to a simulated support surface, or 'outer envelope', of the envelope guide 200 in order to provide an advantageous support for facial tissue. The envelope guide 200 provides an envelope in relation to which the library teeth are to be arranged. The outer envelope can correspond to an internal surface of the facial tissue in a desired rest position against the library tooth 302.

The virtual tooth 302 from the tooth library may be positioned strictly within the outer envelope, as illustrated in FIG. 7C. In other embodiments, the virtual tooth 302 may be positioned crossing the outer envelope. This may be necessary due to a number of reasons, e.g., anatomical or aesthetical reasons, limited number of library teeth, strength of prosthesis, possible position of implants, etc. For automatically positioning of a virtual tooth 302 it may be advantageous to position the tooth 302 within the outer envelope. A manual adjustment may be made from this initial position of virtual tooth 302 during subsequent virtual planning.

Thus, the virtual tooth 302 can be virtually positioned in a desired inclination and with a desired length in relation to the envelope guide, as e.g., shown in FIG. 7C.

This initial position of the virtual tooth 302 may be adjusted to provide an optimal teeth setup. The position, size and/or shape of a library tooth may, for instance, be adjusted for creating a desired smile line. FIGS. 8A, 8B, and 8C illustrate examples of such virtual adjustments of teeth positions in relation to the outer envelope of envelope guide 200. Drag and drop markers may be provided for such virtual adjustments, for instance of an entire teeth setup, as shown by rectangular shapes in FIGS. 8A and 8B, or adjustment of a single tooth, as shown in FIG. 8C.

Adjusting the position of the library tooth can comprise in certain embodiments adjusting an inclination of a longitudinal axis of the library tooth in relation to jaw bone tissue, and adjusting a distance of a coronal end (front end opposite the apical root portion of the tooth) of the library tooth to an outer surface of the jaw bone tissue. The adjustment may be made for creating a desired smile line. Adjustment may alternatively, or in addition, be made of the spatial position, volumetric size, or length of the virtual tooth such that the virtual tooth can be located relative to the outer envelope.

When adjusting the position of a library tooth, it may comprise verifying the position of the at least one library tooth and re-adjusting the position of the at least one library tooth relative to the outer boundary.

Now, a correct rehabilitation position can be determined for the teeth setup and any remaining elements or steps for a dental restoration may be planned from this starting position, such as positioning of dental implants.

As illustrated in FIGS. 9A, 9B, and 9C positions of dental implants 450, as illustrated by the axis 400, 401, 402, 403, 404, and 405, can be adjusted to the position of the teeth in the teeth setup. The position of the teeth setup can be locked and subsequently, at least one dental implant for anchoring a dental restoration based on the teeth setup can be virtually positioned. This may be performed automatically, manually or semi-automatically. This may, for instance, be made in accordance with the disclosure of WO2008/145293 mentioned above.

Production data for manufacturing components related to the dental restoration based on the virtually planned teeth setup can be provided. In FIGS. 10A, 10B, 10C, 10D, 11, and 12 elements are illustrated that can be based on production data provided from the virtual planning, including a try-in prosthesis, temporary prosthesis, or a final soft-tissue supported prosthesis 500, a dental bridge framework 600, and a surgical drill template 700. Some of these elements, such as the pre-denture 500 or the surgical drill template 700 may be produced by rapid prototyping or milling techniques. The pre-denture 500 may be fully automatically produced, and facilitates verification of the dental design. The pre-denture 500 may be proof fitted to a gypsum cast 501 of a jaw of the patient. In certain embodiments, the pre-denture 500 may be proof fitted in the patient to verify a correct position of facial tissue in rest, or a smile line.

Figure 10D:
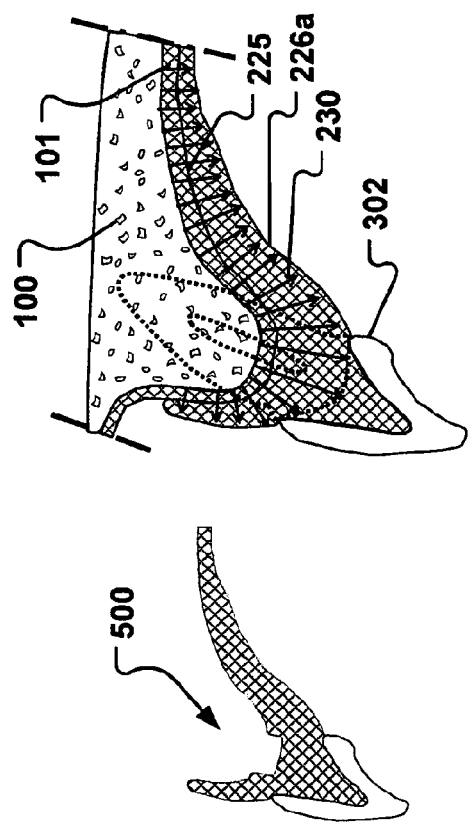
FIGS. 10A, 10B, 10C, 10D, 11, and 12 are perspective views of elements based on example production data provided from the virtually planning, including a try-in prosthesis, a dental bridge framework, and a surgical drill template.
Figure 10C:
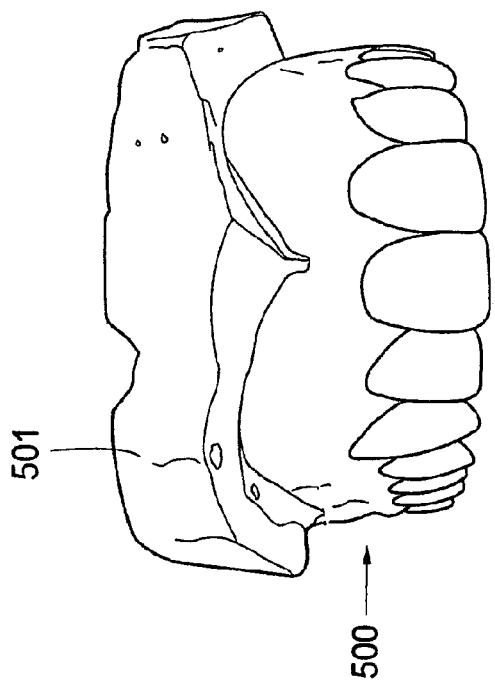
Figure 10A:
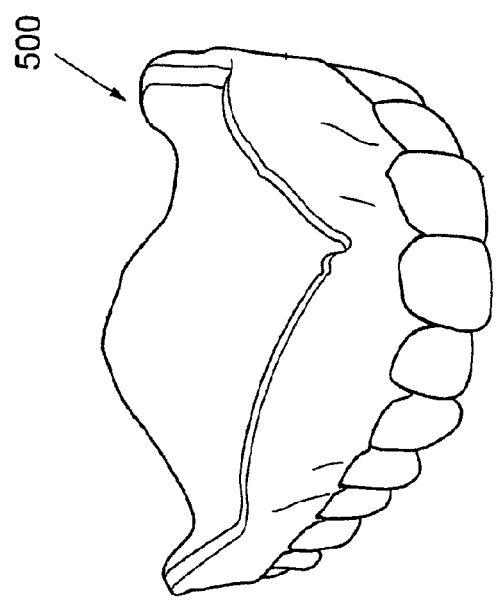
Figure 10B:
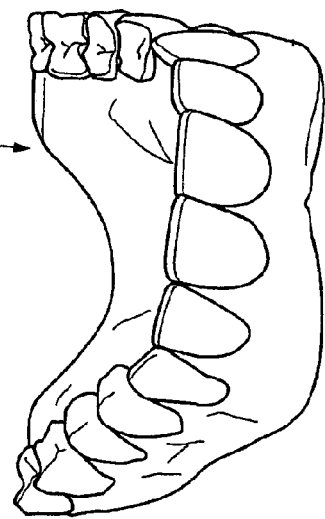
Figure 11:
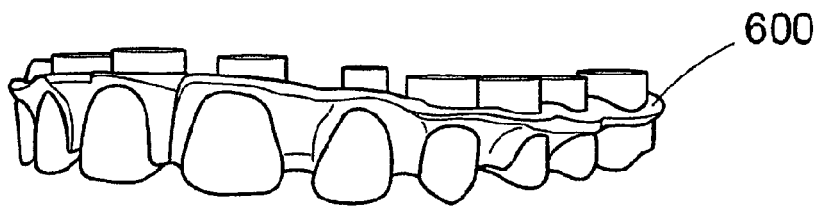
Figure 12:
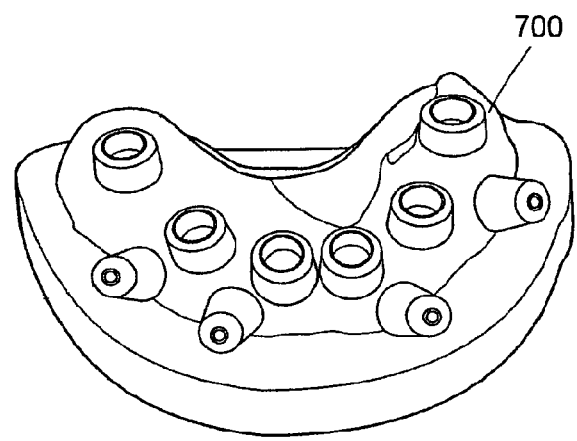

At least a portion of the scan data may be combined with at least a portion of the outer envelope of said desired dental prosthesis. An example is the try-in prosthesis, temporary prosthesis, or a final soft-tissue supported prosthesis 500. Here, a digitized soft-tissue surface, e.g., a patient specific surface, such as based on surface scanned impression, model or intra-oral scanning, can be combined with a CAD object based on the desired dental prosthesis. Two surfaces can be combined, where one surface can be patient specific, for making a prosthesis. The soft tissue data for the corresponding surface of the CAD object may be provided from a library. Alternatively, or in addition, the soft tissue data may be scaled, based on anatomical patient data, such as by morphing, or manual adjustment, such as illustrated on the right in FIG. 10D. As illustrated by arrows 230, the modified soft tissue surfaces, such as surface 226a, can be chosen to compensate for bone resorption of the edentulous maxilla. Thus a natural topography of a soft tissue surface in the oral cavity may be restored by a prosthesis based on the virtual planning. The soft tissue can be restored in relation to the bone surface of the jaw bone, as shown in 10D. The library may comprise one or more objects. The object can be scalable. The objects comprise soft tissue that is scalable. The try-in prosthesis may first be produced and then modified or adopted to the patient. Planning may then be updated based on re-scanning of the try-in prosthesis for providing a final prosthesis. A cross section through a try-in prosthesis is shown to the left in FIG. 10D. The the try-in prosthesis, temporary prosthesis, or a final soft-tissue supported prosthesis 500 may be made integrally in a single monolithic unit. Alternatively, the try-in prosthesis, temporary prosthesis, or a final soft-tissue supported prosthesis 500 may be produced as an assembly of several elements, such as illustrated in FIG. 10D.

Production data for a dental bridge framework can be, for instance, obtained by a cut back technique, e.g., a certain portion of the dental prosthesis is removed starting from the outside of the teeth in order to receive the size and shape of the bridge framework. The portion that has been removed can then be re-created, e.g., by veneering before the bridge framework is installed in the patient and affixed to dental implants.

The teeth chosen from a tooth library may have a known shape. In order to arrive at the shape of the bridge framework shown in FIG. 11, a certain portion of the library teeth may be removed, e.g., the library teeth are cut back in order to arrive at the shape of the bridge framework.

Alternatively or in addition, the bridge framework may be chosen from a library of bridge frameworks. For instance a spline curve (not shown) that follows the teeth set-up may be identified in the computer environment. A bridge framework having the same or a similar spline form may be chosen from the library of bridge frameworks. When the teeth setup is adjusted, this bridge framework chosen from the library of bridge frameworks can be adjusted accordingly.

The connection interface of the bridge framework towards dental implants can be chosen suitably, e.g., a certain type such as a Brånemark System® connection interface, and with a position and orientation towards the dental implants.

Now the CAD object may be provided as production data for producing the bridge framework.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A method of planning a dental prosthesis, said method comprising;
   providing scan data of an anatomical situation of an oral cavity of a patient;
   providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;
   virtually simulating, via a computing environment, a dental prosthesis for supporting facial tissue in said oral cavity based on said scan data;
   from the envelope data, virtually simulating, via the computing environment, the support surface of the envelope portion with respect to said scan data of said oral cavity;
   virtually adjusting, via the computing environment, said simulated dental prosthesis so that a surface of the simulated dental prosthesis corresponds to the simulated support surface of the envelope portion; and
   generating dental prosthesis data based on said virtually adjusted dental prosthesis, wherein said dental prosthesis data is usable for producing said dental prosthesis, wherein said dental prosthesis comprises a virtual tooth, and wherein said virtually adjusting said simulated dental prosthesis comprises virtually adjusting an inclination of a longitudinal axis of a virtual tooth in relation to said simulated support surface of the envelope portion and virtually adjusting a distance of a coronal end of said virtual tooth in relation to said simulated support surface of the envelope portion.

2. The method of claim 1, comprising providing at least one tooth design parameter obtained from said envelope guide, wherein said envelope data comprises tooth design data for said planning of said dental prosthesis.

3. The method of claim 2, wherein said tooth design parameter comprises a desired smile line based on a marking in said envelope guide, and said method comprises providing smile line data for said desired smile line, wherein said smile line data is comprised in said tooth design data obtained from said envelope guide, and adjusting said simulated dental prosthesis relative to said desired smile line.

4. The method of claim 2, wherein said virtually adjusting of said simulated dental prosthesis comprises virtually adjusting a size, shape, inclination, and/or length of a virtual tooth in relation to said tooth design parameter.

5. The method of claim 2, wherein said tooth design parameter comprises a desired tooth position of a virtual tooth of said simulated dental prosthesis, and said method comprises providing tooth position data for said tooth position, including an incisal line position between central incisor teeth and/or a desired position of canines, based on at least one marking in said envelope guide, wherein said tooth position data is comprised in said tooth design data obtained from said envelope guide.

6. The method of claim 1, comprising performing said virtually adjusting said simulated dental prosthesis prior to virtually positioning, which is based on said simulated dental prosthesis, at least one dental implant for anchoring said dental prosthesis.

7. The method of claim 1, comprising identifying anatomically fixed skull reference points, and initially positioning said virtual tooth along a dental arch based on said anatomically fixed skull reference points prior to said adjusting said prosthesis comprising said virtual tooth relative to said simulated support surface of the envelope portion.

8. The method of claim 1, comprising verifying a position of said simulated dental prosthesis and re-adjusting said position of said simulated dental prosthesis relative to said simulated support surface of the envelope portion.

9. The method of claim 1, wherein said envelope data of said envelope guide has a fixed spatial relation to said scan data based on interfacing complementary surfaces of said envelope guide and said oral cavity.

10. The method of claim 1, wherein said virtually adjusting said simulated dental prosthesis relative to said simulated support surface of the envelope portion comprises virtually adjusting at least a portion of said simulated dental prosthesis to be located within a virtual space defined by said simulated support surface of the envelope portion.

11. The method of claim 1, further comprising combining at least a portion of said scan data with at least a portion of said simulated dental prosthesis.

12. The method of claim 1, further comprising designing a framework for the envelope guide based on at least a portion of said scan data, and optionally including said framework with at least one anchoring element extending in a first direction for anchoring said envelope portion.

13. A method of providing production data for a component related to a dental prosthesis, comprising said method of planning said dental prosthesis of claim 1, and providing dental prosthesis data as production data based on said planning for producing at least a portion of said dental prosthesis or components related thereto.

14. A system for planning a dental prosthesis in a patient, said system comprising a processing unit adapted to
- process scan data of an anatomical situation of an oral cavity of a patient;
- process envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;
- virtually simulate a dental prosthesis for supporting facial tissue in said oral cavity based on said scan data;
- from the envelope data, virtually simulate the support surface of the envelope portion with respect to said scan data of said oral cavity;
- virtually adjust said simulated dental prosthesis so that a surface of the simulated dental prosthesis corresponds to the simulated support surface of the envelope portion with respect to said oral cavity; and
- generate dental prosthesis data based on said virtually adjusted dental prosthesis, wherein said dental prosthesis data is usable for producing said dental prosthesis,
- wherein said dental prosthesis comprises at least one of a virtual tooth or a simulated soft tissue surface,
- wherein said virtually adjust of said simulated dental prosthesis comprises
  - virtually adjust a distance of a coronal end of said virtual tooth in relation to said simulated support surface of the envelope portion.

15. A non-transitory computer readable medium containing program instructions for planning a dental prosthesis in a patient, wherein execution of the program instructions by a computer environment carries out a method, comprising:
- processing scan data of an anatomical situation of an oral cavity of a patient;
- processing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;
- virtually simulating a dental prosthesis for supporting facial tissue in said oral cavity based on said scan data;
- from the envelope data, virtually simulating the support surface of the envelope portion with respect to said scan data of said oral cavity;
- virtually adjusting said simulated dental prosthesis so that a surface of the simulated dental prosthesis corresponds to the simulated support surface of the envelope portion with respect to said oral cavity; and
- generating dental prosthesis data based on said virtually adjusted dental prosthesis, wherein said dental prosthesis data is usable for producing said dental prosthesis,
- wherein said dental prosthesis comprises at least one of a virtual tooth or a simulated soft tissue surface,
- wherein said virtually adjusting said simulated dental prosthesis comprises
  - virtually adjusting a distance of a coronal end of said virtual tooth in relation to said simulated support surface of the envelope portion.

16. The method of claim 1, further comprising:
- virtually simulating the oral cavity based on the scan data; and
- virtually simulating the support surface in the simulated oral cavity based on the envelope data.

17. The method of claim 1, wherein the envelope guide is made of wax, polymer material or a combination thereof.

18. The method of claim 1, further comprising digitizing the envelope guide by at least one of a surface scanner, x-ray imager and volumetric scanner so as to provide surface position and orientation as envelope data.

19. The method of claim 1, further comprising positioning in the oral cavity of the patient said envelope guide comprising the envelope portion having the support surface arranged to support facial tissue of the patient in a desired position.

20. The method of claim 19, further comprising scanning the patient wearing the envelope guide so as to generate the envelope data.

21. The method of claim 1, further comprising producing said dental prosthesis based on the generated dental prosthesis data.

22. The method of claim 1, wherein the facial tissue of the patient in a desired position is the facial tissue in a position desired by the patient at the completion of treatment.

23. The method of claim 1, wherein the envelope guide covers a bite portion of a tooth or dental prosthesis.

24. The method of claim 1, wherein the envelope guide comprises a lip support surface.

25. The method of claim 1, wherein the support surface corresponds to an internal surface of the facial tissue in a desired rest position against a tooth or virtual tooth.

26. The method of claim 1, wherein a desired position of the facial tissue provides an aesthetically correct appearance when the facial tissue is at rest and when the patient is smiling.

27. A method of planning a dental prosthesis, said method comprising:
- providing scan data of an anatomical situation of an oral cavity of a patient;
- providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;
- virtually simulating, via a computing environment, a dental prosthesis for supporting facial tissue in said oral cavity based on said scan data;
- from the envelope data, virtually simulating, via the computing environment, the support surface of the envelope portion with respect to said scan data of said oral cavity;
- virtually adjusting, via the computing environment, said simulated dental prosthesis so that a surface of the simulated dental prosthesis corresponds to the simulated support surface of the envelope portion; and
- generating dental prosthesis data based on said virtually adjusted dental prosthesis, wherein said dental prosthesis data is usable for producing said dental prosthesis,
- wherein said dental prosthesis comprises a virtual tooth, and wherein said virtually adjusting said simulated dental prosthesis comprises virtually adjusting a distance of a coronal end of said virtual tooth in relation to said simulated support surface of the envelope portion.

28. A method of planning a dental prosthesis, said method comprising:
- providing scan data of an anatomical situation of an oral cavity of a patient;
- providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;

virtually simulating, via a computing environment, a dental prosthesis for supporting facial tissue in said oral cavity based on said scan data;

from the envelope data, virtually simulating, via the computing environment, the support surface of the envelope portion with respect to said scan data of said oral cavity;

virtually adjusting, via the computing environment, said simulated dental prosthesis so that a surface of the simulated dental prosthesis corresponds to the simulated support surface of the envelope portion; and generating dental prosthesis data based on said virtually adjusted dental prosthesis, wherein said dental prosthesis data is usable for producing said dental prosthesis, wherein said dental prosthesis comprises a virtual tooth, and wherein said virtually adjusting said simulated dental prosthesis comprises virtually adjusting a spatial position, volumetric size, shape, length, thickness, or width of said virtual tooth relative to said simulated support surface of the envelope portion and virtually adjusting a distance of a coronal end of said virtual tooth in relation to said simulated support surface of the envelope portion.

29. A method of planning a dental prosthesis, said method comprising:

providing scan data of an anatomical situation of an oral cavity of a patient;

providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;

virtually simulating, via a computing environment, a dental prosthesis for supporting facial tissue in said oral cavity based on said scan data;

from the envelope data, virtually simulating, via the computing environment, the support surface of the envelope portion with respect to said scan data of said oral cavity;

virtually adjusting, via the computing environment, said simulated dental prosthesis so that a surface of the simulated dental prosthesis corresponds to the simulated support surface of the envelope portion; and generating dental prosthesis data based on said virtually adjusted dental prosthesis, wherein said dental prosthesis data is usable for producing said dental prosthesis, wherein said dental prosthesis comprises a simulated soft tissue surface, and wherein said virtually adjusting said simulated dental prosthesis comprises virtually adjusting an inclination of a longitudinal axis of a virtual tooth in relation to said simulated support surface of the envelope portion and virtually adjusting a distance of a coronal end of said virtual tooth in relation to said simulated support surface of the envelope portion.

30. A method of planning a dental prosthesis, said method comprising:

providing scan data of an anatomical situation of an oral cavity of a patient;

providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;

virtually simulating, via a computing environment, a dental prosthesis for supporting facial tissue in said oral cavity based on said scan data;

from the envelope data, virtually simulating, via the computing environment, the support surface of the envelope portion with respect to said scan data of said oral cavity;

virtually adjusting, via the computing environment, said simulated dental prosthesis so that a surface of the simulated dental prosthesis corresponds to the simulated support surface of the envelope portion; and generating dental prosthesis data based on said virtually adjusted dental prosthesis, wherein said dental prosthesis data is usable for producing said dental prosthesis, wherein said dental prosthesis comprises a virtual tooth, and wherein said virtually adjusting said simulated dental prosthesis comprises virtually adjusting a spatial position, volumetric size, shape, length, thickness, or width of said virtual tooth relative to said simulated support surface of the envelope portion and virtually adjusting a distance of a coronal end of said virtual tooth in relation to said simulated support surface of the envelope portion.

31. A method of planning a dental prosthesis, said method comprising:

providing scan data of an anatomical situation of an oral cavity of a patient;

providing envelope data of an envelope guide, said envelope guide comprising an envelope portion having a support surface arranged to support facial tissue of the patient in a desired position when the envelope guide is positioned in said oral cavity of said patient, wherein the facial tissue includes lip and/or cheek tissue, and not dental soft tissue surrounding bone and dentition;

virtually simulating, via a computing environment, a dental prosthesis for supporting facial tissue in said oral cavity based on said scan data;

from the envelope data, virtually simulating, via the computing environment, the support surface of the envelope portion with respect to said scan data of said oral cavity;

virtually adjusting, via the computing environment, said simulated dental prosthesis so that a surface of the simulated dental prosthesis corresponds to the simulated support surface of the envelope portion; and generating dental prosthesis data based on said virtually adjusted dental prosthesis, wherein said dental prosthesis data is usable for producing said dental prosthesis, wherein said dental prosthesis comprises a simulated soft tissue surface, and wherein said virtually adjusting said simulated dental prosthesis comprises virtually adjusting a spatial position, volumetric size, shape, length, thickness, or width of said virtual tooth relative to said simulated support surface of the envelope portion and virtually adjusting a distance of a coronal end of said virtual tooth in relation to said simulated support surface of the envelope portion.

32. The system of claim 14, wherein the processing unit is further adapted to provide at least one tooth design parameter obtained from said envelope guide, wherein said envelope data comprises tooth design data for said planning of said dental prosthesis.

33. The system of claim 32, wherein said tooth design parameter comprises a desired tooth position of a virtual tooth of said simulated dental prosthesis, and wherein the processing unit is further adapted to provide tooth position data for said tooth position, including an incisal line position between central incisor teeth and/or a desired position of canines, based on at least one marking in said envelope guide, wherein said tooth position data is comprised in said tooth design data obtained from said envelope guide.

34. The system of claim 14, wherein said envelope data of said envelope guide has a fixed spatial relation to said scan data based on interfacing complementary surfaces of said envelope guide and said oral cavity.

35. The computer readable medium of claim 15, further comprising providing at least one tooth design parameter obtained from said envelope guide, wherein said envelope data comprises tooth design data for said planning of said dental prosthesis.

36. The computer readable medium of claim 35, wherein said tooth design parameter comprises a desired tooth position of a virtual tooth of said simulated dental prosthesis, and said method comprises providing tooth position data for said tooth position, including an incisal line position between central incisor teeth and/or a desired position of canines, based on at least one marking in said envelope guide, wherein said tooth position data is comprised in said tooth design data obtained from said envelope guide.

37. The computer readable medium of claim 15, wherein said envelope data of said envelope guide has a fixed spatial relation to said scan data based on interfacing complementary surfaces of said envelope guide and said oral cavity.

* * * * *